United States Patent [19]

Piwinski et al.

[11] Patent Number: 4,596,791
[45] Date of Patent: Jun. 24, 1986

[54] COMPOUNDS FOR TREATING HYPERTENSION

[75] Inventors: John J. Piwinski, Port Chester, N.Y.; John T. Suh, Greenwich, Conn.; Paul Menard, Tuckahoe; Howard Jones, Ossining, both of N.Y.; Edward S. Neiss, New Canaan, Conn.

[73] Assignee: USV Pharmaceutical Corp., Tarrytown, N.Y.

[21] Appl. No.: 690,387

[22] Filed: Jan. 10, 1985

Related U.S. Application Data

[63] Continuation of Ser. No. 475,804, Mar. 16, 1983, abandoned.

[51] Int. Cl.$^4$ .......................... H61K 37/64; C07K 5/06
[52] U.S. Cl. ...................................... 514/19; 530/800; 260/998.2
[58] Field of Search ...................... 562/450; 514/2, 19; 260/112.5 R

[56] References Cited

U.S. PATENT DOCUMENTS

| | | | |
|---|---|---|---|
| 4,350,704 | 9/1982 | Hoefle et al. | 424/274 |
| 4,370,494 | 1/1983 | Wright et al. | 562/450 |
| 4,374,829 | 2/1983 | Harris et al. | 514/19 |
| 4,474,692 | 10/1984 | Oka et al. | 260/112.5 R |
| 4,482,544 | 11/1984 | Huang et al. | 260/112.5 R |
| 4,496,542 | 1/1985 | Skiles et al. | 514/2 |

FOREIGN PATENT DOCUMENTS

| | | | |
|---|---|---|---|
| 0050800 | 5/1982 | European Pat. Off. | 260/112.5 R |
| 2095682 | 10/1983 | United Kingdom | 260/112.5 R |

OTHER PUBLICATIONS

Tetrahedron Letters, vol. 23, No. 39, pp. 3995–3998 (1982).
Bull. Chem. Soc. Jpn. 53, 3661–3669 (1980).
Biochem. and Biophys. Res. Commun. (1981), 963–969, vol. 102, No. 3.

Primary Examiner—Delbert R. Phillips

[57] ABSTRACT

Compounds of the formula $$\begin{array}{c} A_1 \\ \phantom{A_1}\diagdown \\ \phantom{AAA}Q-(CH_2)_m-CH-NH-\overset{R_1}{\underset{\underset{\underset{Y_1}{|}}{\underset{C=O}{|}}}{C}}-\overset{O}{\underset{\underset{M_3}{|}}{\underset{Z_3}{|}}}-N-\overset{R_2}{\underset{\underset{M_1}{|}}{\underset{Z_1}{|}}}-\overset{O}{\underset{\underset{M_2}{|}}{\underset{Z_2}{|}}}-Y_2 \\ \phantom{A}\diagup \\ A_2 \end{array}$$

and their pharmaceutically acceptable salts, wherein the substituents are as defined herein, having antihypertensive activity.

7 Claims, No Drawings

COMPOUNDS FOR TREATING HYPERTENSION

This application is a continuation of our previous copending application Ser. No. 475,804 filed Mar. 16, 1983 now abandoned.

BACKGROUND OF THE INVENTION

This application relates to compounds, their pharmaceutically acceptable salts, and pharmaceutical preparations made therefrom, having utility in the treatment of hypertension in subjects suffering therefrom.

SUMMARY OF THE INVENTION

Broadly stated, the present invention comprises compounds of the formula

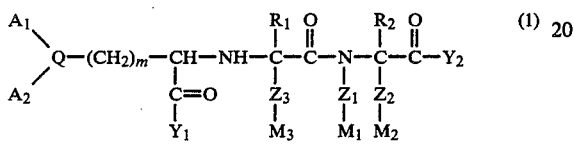

and pharmaceutically acceptable salts thereof, wherein
$A_1$ and $A_2$ are independently hydrogen, halogen, hydroxy, alkyl, alkoxy, or trifluoromethyl;
Q is phenyl or fused arylcycloalkyl;
m is 0 to 3 inclusive;
$Y_1$ and $Y_2$ are independently —OR or

$R_1$ and $R_2$ are independently R, cycloalkyl, or aminoalkyl,
wherein $Z_1$, $Z_2$, and $Z_3$, reading toward the $M_i$ substituent, are selected from the group consisting of
—(CH$_2$)$_n$—,          —NHCH$_2$(CH$_2$)$_n$—,
—NHCH$_2$(CH$_2$)$_n$NH—,    —(CH$_2$)$_n$SO$_2$—,
—(CH$_2$)$_n$N(R)SO$_2$—,

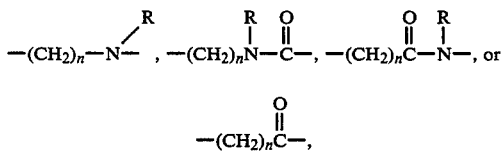

in which n is 0 to 6 inclusive,
$M_1$, $M_2$, and $M_3$ are independently selected from the group consisting of hydrogen, alkyl, cycloalkyl, aryl, fused polycyclic aryl, or fused cycloalkylaryl, wherein up to 3 carbon atoms of $M_1$, $M_2$ and $M_3$ can be oxidized to —C(O)— or replaced by —NH—, —O—, —S—, =N—, or —SO$_2$—; wherein each of $M_1$, $M_2$ and $M_3$ is unsubstituted or has up to three substituents selected from the group consisting of halogen, alkyl, aminoalkyl, aralkyl, cycloalkyl, nitroalkylamino, acylamino, acylaminoalkyl, acylaminoalkylamino, trifluoromethyl, nitro, cyano, —OR, —SR, —C(O)OR, —S(O)R, —SO$_2$R,

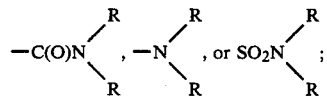

wherein when $M_3$ is substituted aryl, $Z_1M_1$, and $Z_2M_2$ can be linked together to form an alkylene bridge up to 6 carbon atoms in length which is optionally substituted with lower alkyl or fused with an aryl ring;
wherein in each occurrence R is independently hydrogen, alkyl, cycloalkyl, aryl, aralkyl, heteroalkyl, heteroaralkyl, or heteroaryl;
provided that at least one of $M_1$, $M_2$ and $M_3$ is an aryl ring, or has an aryl moiety, in which the aryl ring or moiety has two or three substituents other than hydrogen;
wherein the alkyl groups and the alkyl moieties contain up to 9 carbon atoms, the cycloalkyl groups and moieties are saturated or unsaturated and contain 3 to 12 atoms, and the aryl rings contain up to 12 atoms.

DESCRIPTION OF THE PREFERRED EMBODIMENTS

Preferred compounds of the present invention include those of the general formula given above in which $Y_1$ and $Y_2$ are each hydroxy, benzyloxy, or lower alkoxy; $R_1$ and $R_2$ are each hydrogen, alkyl, aryl, aralkyl, cycloalkyl, or w-amino ("omega-amino")alkyl wherein the amino is mono- or disubstituted with hydrogen, alkyl, aryl, or aralkyl, or is incorporated in a saturated or unsaturated one- or two-ring heterocyclic moiety containing preferably up to 12 atoms in the ring; m is 1 or 2; $A_1$ and $A_2$ are hydrogen or lower alkyl; and Q is phenyl or indanyl.

The alkyl groups per se and the alkyl moieties in alkoxy, aralkyl, cycloalkyl, aminoalkyl, and the like, may be straight-chained or branched and preferably contain from 1 to 9 carbon atoms. Such groups include methyl, ethyl, propyl, isopropyl, butyl, isobutyl, tertiary-butyl, amyl, iso-amyl, hexyl, octyl, and the like. Preferably the alkyl groups are lower alkyl, which term shall refer to alkyl groups containing from 1 to 6 carbon atoms, straight-chained or branched. The cycloalkyl groups and moieties are saturated or unsaturated and contain 3 to 12 carbon atoms and preferably 3 to 9 carbon atoms.

Preferred structures include those in which $Z_1$, $Z_2$ and/or $Z_3$ is a chemical bond, so that at least one component M is connected directly to the rest of the molecule, and those within the above general definition in which n is 0, 1, 2, 3, or 4, and R is hydrogen or lower alkyl.

Preferred structures for the $M_1$, $M_2$ and $M_3$ groups include hydrogen, cycloalkyl, alkyl, aryl, fused arylcycloalkyl, heteroaryl, and fused aryl-heterocycloalkyl.

Preferred cyclic and polycyclic ring structures, including those falling within the definition of $M_1$, $M_2$, and $M_3$, contain up to 20 carbon atoms and include such radicals as cyclopropyl, cyclobutyl, cyclopentyl, cyclohexyl, cycloheptyl, adamantyl, norbornyl, phenyl, tolyl, benzyl, phenethyl, indolyl, hydroxybenzyl, indanyl, naphthyl, tetrahydronaphthyl, decanhydronaphthyl, pyridyl, quinolyl, isoquinolyl, guanidino, pyrrolidyl, pyrrolyl, morpholinyl, furyl, furfuryl, tetrahydrofurfuryl, benzimidazolyl, thienyl, imidazolyl, tetrahydroisoquinolyl,

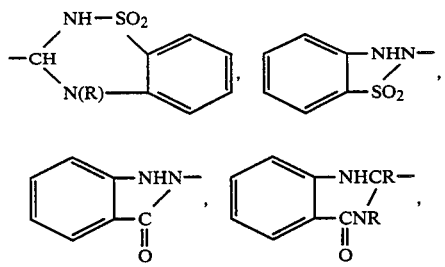

and the like, specifically including all isomers of radicals named herein that have more than one isomer. The cycloalkyl, aryl, and fused aryl-cycloalkyl structures can also contain one or more, preferably up to three, hetero atoms, i.e., sulfur, oxygen, or nitrogen atoms, thereby forming a hetero-ring.

At least one, and preferably one, of $M_1$, $M_2$ and $M_3$ is aryl or has an aryl moiety, in which the aryl group or moiety carries two or three substituents other than hydrogen. Such an Mi group is preferably connected to the main chain by non-labile bonds, so that the molecule (1) resists cleavage in the stomach and is thus intact when it enters the blood, which enhances the therapeutic effect and duration of the compound and may reduce undesirable side-effects. Structures having an aryl moiety include aryl containing one or more hetero atoms, polycyclic aryl, polycyclic aryl containing one or more hetero atoms, fused arylcycloalkyl, and fused arylcycloalkyl containing one or more hetero atoms. Preferred structures include those in the above list of cyclic and polycyclic structures which have an aryl ring of six carbon atoms. Preferred substituents for the aryl ring include halogen, nitro, lower alkyl, —COOH, carboxy-lower alkoxy, phenoxy and hydroxy; sulfamoyl which is optionally substituted with alkyl; and amino which is optionally substituted with lower alkyl, phenyl, phenyl-lower alkyl, heteroaryl-lower alkyl, nitro-lower alkyl, lower alkyl-carbonyl, and lower alkyl-carbonyl-aminoalkyl, (e.g., $CH_3C(O)NH(CH_2)_{2-4}NH$—, $CH_3C(O)NH$—, and furfurylamino).

When $M_3$ has a substituted aryl moiety, —$Z_1M_1$ and —$Z_2M_2$ can be linked to form an alkylene (i.e. —($CH_2)_n$—) bridge 3, 4, 5 or 6 carbon atoms in length. Preferably the alkylene bridge forms a proline ring with the nitrogen and carbon atoms to which $Z_1$ and $Z_2$ are respectively attached. The alkylene bridge is optionally substituted with lower alkyl. The alkylene bridge can also be fused with an aryl ring; a preferred example is where —$Z_1M_1$ and —$Z_2M_2$ form a tetrahydroisoquinoline ring, i.e.,

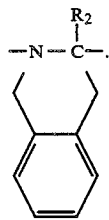

In notation such as

in which R is written twice we intend to indicate that each R can be any of the substituents listed hereinabove for R.

The halo groups include fluoro, chloro, bromo and iodo. Preferred hetero atoms are S, O, and N. Preferred acyl groups are lower alkyl-carbonyl, and aryl-carbonyl.

Preferred compounds are those in which at least one, and more preferably both of $R_1$ and $R_2$ are hydrogen or lower alkyl.

Compounds in accordance with the present invention are readily prepared employing known starting materials and procedures. It will be understood by those skilled in the art that the carbon atoms to which $R_1$ and

are attached can be asymmetric centers, such that the inventive compounds may exist in (R,R), (R,S), (S,R), and (S,S) forms. The carbon atom to which $R_2$ is attached can also be an asymmetric center. Individual isomers and diastereo-isomeric mixtures of said forms are within the scope of the invention. The preferred forms have (S,S) or (S,S,S) configuration.

The compounds of the formula (1) can be prepared by reacting a compound of the formula (2):

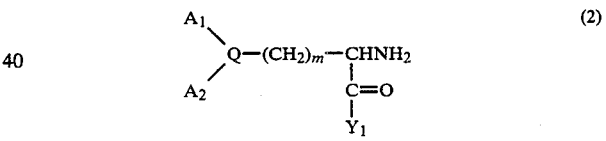

with compound (3):

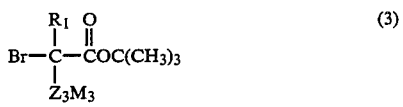

wherein $A_1$, $A_2$, m, $Y_1$, $R_1$, $Z_3$ and $M_3$ are as defined hereinabove, except that $Y_1$ is preferably ethoxy to protect against unwanted bond formation at the $Y_1$ site. The product of reacting compounds (2) and (3), which is compound (4),

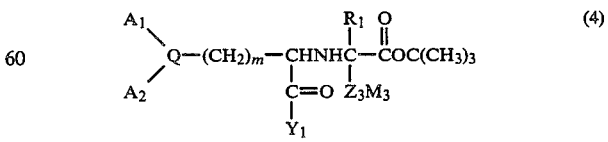

is reacted with 2,2,2-trichloroethyl chloroformate to protect the nitrogen atom, and the N-protected product is reacted with strong HCl to remove the t-butyl esterifying group to form compound (5):

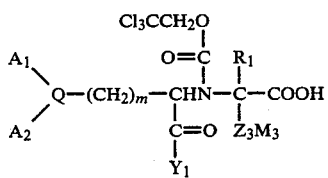

Compound (5) is reacted with compound (6):

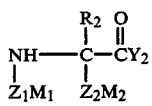

The reaction can be carried out by converting compound (5) to the acid chloride by reaction with oxalyl chloride, and then adding compound (6). Alternatively, compounds (4) and (6) can be condensed directly, following hydrolysis of the t-butyl ester to the acid, in the presence of a suitable coupling agent such as DCC (dicyclohexylcarbodiimide) or CDI (N,N'-carbonyldiimidazole) in a reaction familiar to those of ordinary skill in the peptide synthesis art. While proceeding via a coupling agent is preferred when the reaction can be made to proceed with a yield higher than that provided by the corresponding acid chloride route, this route's likelihood of success is often determined on a case-by-case basis; thus, in an overall sense the acid chloride route is preferred except where the direct-coupling route is found to work better.

Compound (6) can be prepared by procedures within the skill of the art. For instance, the amino acid

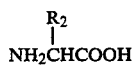

can be N-protected with a carbonylbenzyloxy or similar protecting group, then substituted with the desired $Z_2M_2$ at the alpha-carbon. The nitrogen is then de-protected and substituted with the desired $Z_1M_1$ group, and the resultant compound is reacted with compound (5) to give compound (7):

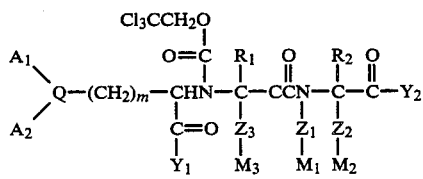

Compound (7) is de-N-protected with zinc in acetic acid, and then, if desired, ester groups such as in the $Y_1$ and/or $Y_2$ position are converted to the free acid with commonly known reagents such as HCl or NaOH. As can be seen in the accompanying Examples, methods are known for converting some but not all of the esterified groups to the acid. Each of the above reactions proceeds in a straightforward manner in a suitable solvent at temperatures ranging from 0° C. to 150° C.

The reaction products are sometimes obtained as a mixture of diasteroisomers which can be separated by standard methods of fractional crystallization or chromatography.

The compounds of this invention form acid salts with various inorganic and organic acids which are also within the scope of the invention. The pharmaceutically-acceptable acid addition salts of the compounds of the present invention may be prepared by conventional reactions by reacting the free amino acid or amino ester with an appropriate acid providing the desired anion, either in a solvent or medium in which the salt is insoluble, or in water and removing the water by freeze-drying. The salts of strong acids are preferred. As exemplary, but not limiting, of pharmaceutically-acceptable acid salts are the salts of hydrochloric, hydrobromic, sulfuric, nitric, acetic, fumaric, malic, maleic and citric acids.

The action of the enzyme renin or angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds within the scope of this invention which intervene in the renin-to-angiotensin I-to-angiontensin II sequence inhibit angiotensin I converting enzyme and therefore are useful in reducing or relieving hypertension. Furthermore, the compounds within the scope of the present invention which possess diuretic activity promote relief from hypertension by promoting diuresis, and consequently have utility in treating congestive heart failure. Compounds within the scope of the present invention can also simultaneously possess ACE inhibitory and diuretic activity, which is particularly unexpected in view of the fact that such simultaneous activity cannot be predicted from prior art compounds. Thus by the administration of a composition containing one or a combination of compounds of formula (1) or pharmaceutically-acceptable salts thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day, is appropriate to reduce blood pressure. The substance is preferably administered orally, but a parenteral route such as subcutaneously, intramuscularly, intravenously or intraperitonealy can also be employed.

The compounds of the invention can be utilized to achieve the reduction of blood pressure by formulating one or more of them in compositions such as tablets, capsules or elixirs for oral administration or in sterile solutions or suspensions for parenteral administration. About 10 to 500 mg of a compound or mixture of compounds of formula (1) or physiologically acceptable salt(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservatives, antioxidants and the like can be incorporated as required.

Specific embodiments of the invention are illustrated in the following Examples.

EXAMPLE 1

A mixture of 25.3 gm (0.141 mol) of L-2-amino-4-phenylbutyric acid (I-A) in 400 ml of 5N ethanolic hydrogen chloride was stirred at room temperature for 7 days. The reaction mixture was concentrated in vacuo and the product triturated with ether. The white solid was filtered off, dissolved in a saturated solution of aqueous potassium carbonate, and extracted twice with ethyl acetate. The organic portions were combined, washed once with brine, dried over magnesium sulfate, filtered, and concentrated in vacuo to give 23.6 gm (81%) of ethyl L-2-amino-4-phenylbutyrate (I-B) as an oil: $[\alpha]_D^{MEOH} = +35.5°$.

A mixture containing 96.2 gm (0.629 mol) of 2-bromopropionic acid, 64.0 gm (0.592 mol) of benzyl alcohol, and 2 ml of concentrated sulfuric acid in 200 ml of methylene chloride was refluxed for 22 hours. The reaction mixture was cooled to room temperature and washed successively with water, saturated aqueous potassium carbonate, saturated aqueous sodium bicarbonate, and water. It was then dried over magnesium sulfate, filtered, concentrated in vacuo and distilled via short path to give a fraction (bp 90°–110° C.; 0.1 mm Hg) containing 62.1 gm (43%) of benzyl 2-bromopropionate (I-C) as an oil.

A mixture of 9.6 gm (0.046 mol) of compound (I-B), 17.0 gm (0.069 mol) of compound (I-C), and 7.0 ml (0.050 mol) of triethylamine in 100 ml of acetonitrile was refluxed for 12 hours. The reaction mixture was filtered and concentrated in vacuo. The residue was taken up in ether and washed with a saturated aqueous solution of sodium bicarbonate and with brine. It was dried over magnesium sulfate, filtered, concentrated in vacuo, and the residue chromatographed via HPLC [Water's 500, 10% ethyl acetate in hexanes] to give N-[(1S)-1-ethoxycarbonyl-3-phenylpropyl]-D-alanine benzyl ester followed by 4.6 gm (27%) of N-[(1S)-1-ethoxycarbonyl-3-phenylpropyl]-L-alanine benzyl ester (I-D) as oils.

A mixture of 5.40 gm (14.6 mmol) of compound (I-D) and 1.0 gm of 10% palladium on activated carbon in 300 ml of absolute ethanol was hydrogenated at 40 psi for 2 hours. The mixture was filtered and the filtrate concentrated in vacuo. The residue was triturated with pentane and filtered to give 3.25 gm (80%) of N-[(1S)-1-ethoxycarbonyl-3-phenylpropyl]-L-alanine (I-E) as a white solid: mp 147°–148° C.

To a vigorously stirred solution of 50 ml (1.58 mol) of anhydrous hydrazine in 5 liters of ether at room temperature was added portionwise 32.5 gm (0.128 mol) of 4-chloro-3-sulfamoylbenzoyl chloride. After 2 hours the mixture was allowed to settle and the supernatant was decanted. The residue was then dissolved in 300 ml of hot water. The hot solution was filtered and the filtrate cooled overnight. The precipitate was filtered off, washed with ether, and dried in vacuo to give 10.2 gm (32%) of 4-chloro-3-sulfamoylbenzoyl hydrazide (I-F) as a white crystalline solid: mp 228°–231° C.

To a stirred suspension containing 14.5 gm (58.1 mmol) of compound (I-F) and 8.04 gm (58.2 mmol) of potassium carbonate in 60 ml of N,N-dimethylformamide at 0° C. was added dropwise over 1 hour 9.59 ml (59.4 mmol) of t-butyl bromoacetate. After stirring for 1 hour at room temperature the reaction mixture was poured into 500 ml of water and extracted three times with ethyl acetate. The combined organic portions were dried over magnesium sulfate, filtered, and concentrated in vacuo. The product was chromatographed via HPLC [Water's 500, 72% ethyl acetate in hexanes, k'=5.5] to afford a solid product, which upon recrystallization from ethyl acetate/hexanes gave 5.75 gm (27%) of 1-t-butylcarboxymethyl-2-(4-chloro-3-sulfamoylbenzoyl)hydrazine (I-G) as a white crystalline solid: mp 125°–128° C.

To a solution containing 0.84 gm (3.0 mmol) of compound (I-E), 1.09 gms (2.98 mmol) of compound (I-G), and 0.811 gm (5.29 mmol) of 1-hydroxybenzotriazole hydrate in 25 ml of dry tetrahydrofuran at 0° C. and under an atmosphere of nitrogen was added dropwise a solution of 0.62 gm (3.0 mmol) of N,N'-dicyclohexylcarbodiimide in 10 ml of dry tetrahydrofuran. The reaction mixture was then allowed to gradually warm to room temperature. After 1.5 hours 0.40 ml (2.9 mmol) of triethylamine was added dropwise to the solution. The mixture was then allowed to stir overnight, after which it was filtered and concentrated in vacuo. The residue was taken up in ethyl acetate and washed twice with a saturated aqueous solution of sodium bicarbonate and once each with water and brine. The organic phase was dried over magnesium sulfate, filtered, and concentrated in vacuo. The product was chromatographed via HPLC [Water's 500, 35% methylene chloride in ether, k'=4.9] to yield 424 mg (23%) of 1-[N-[(1S)-1-ethoxycarbonyl-3-phenylpropyl]-L-alanyl]-1-t-butylcarboxymethyl-2-(4-chloro-3-sulfamoylbenzoyl)hydrazine (I-H) as a glass.

A mixture containing 420 mg (0.672 mmol) of compound (I-H) in 15 ml of 4N hydrogen chloride in dioxane was stirred for 15.5 hours at room temperature. The mixture was concentrated in vacuo and the residue triturated with ether and filtered to give 408 mg (100%) of 1-[N-[(1S)-1-ethoxycarbonyl-3-phenylpropyl]-L-alanyl]-1-carboxymethyl-2-(4-chloro-3-sulfamoylbenzoyl)hydrazine hydrochloride (I-I) as a white solid: mp 144° C. (softens).

(I-E) + (I-G) 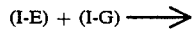

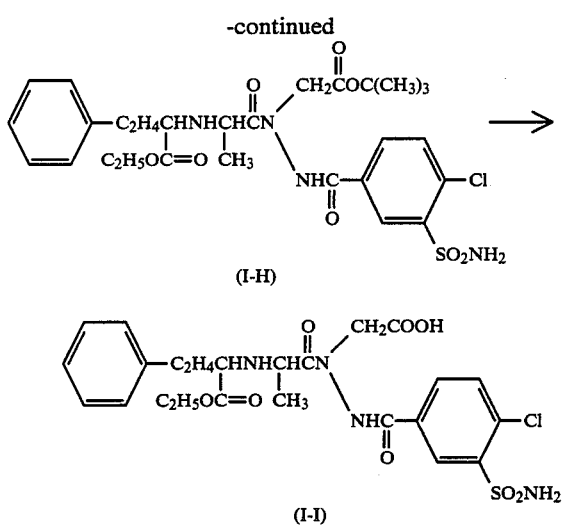

(I-H)

(I-I)

EXAMPLE II

To a mixture of 122.6 gm (0.801 mol) of 2-bromo propionic acid and 2.5 ml of concentrated sulfuric acid in 400 ml of methylene chloride at −78° C. and under an atmosphere of nitrogen was bubbled 300 ml of isobutylene. The reaction mixture was slowly allowed to warm to room temperature. After 22 hours the mixture was concentrated in vacuo and the residue taken up in ether and washed three times with a saturated aqueous solution of sodium carbonate and once with brine. It was dried over magnesium sulfate, filtered, and concentrated in vacuo to yield 104.9 gm (63%) of t-butyl 2-bromopropionate (II-A) as an oil.

A mixture of 24.0 gm (0.116 mol) of compound (I-B), 31.1 gms (0.148 mol) of compound (II-A), and 18.0 ml (0.129 mol) of triethylamine in 200 ml of acetonitrile was refluxed for 10 hours. The reaction mixture was filtered and concentrated in vacuo. The residue was taken up in ether and washed twice with water, once with a saturated aqueous solution of potassium carbonate, once with water again, and once with brine. It was dried over magnesium sulfate, filtered, concentrated in vacuo, and chromatographed via HPLC [Water's 500, 10% ethyl acetate in hexanes] to give 11.83 gms (31%) of N-[(1S)-1-ethoxycarbonyl-3-phenylpropyl]-D-alanine t-butyl ester ($k'=2.6$) and 15.75 gm (41%) of N-[(1S)-1-ethoxycarbonyl-3-phenylpropyl]-L-alanine t-butyl ester (II-B) ($k'=4.0$).

A mixture of 10.00 gm (29.81 mmol) of compound (II-B), 4.00 ml (49.5 mmol) of pyridine and 4.40 ml (32.0 mmol) of 2,2,2-trichloroethyl chloroformate in 75 ml of dry tetrahydrofuran under an atmosphere of nitrogen was refluxed for 3.5 hours. The reaction mixture was filtered and concentrated in vacuo. The residue was taken up in ether and washed four times with 1N aqueous hydrochloric acid and once with brine. The organic phase was dried over magnesium sulfate, filtered, and concentrated in vacuo. The product was chromatographed via HPLC [Water's 500, 15% ether in hexanes, $k'=2.4$] to afford 13.78 gm (90%) of N-[(1S)-1-ethoxycarbonyl-3-phenylpropyl]-N-(2,2,2-trichloroethoxycarbonyl)-L-alanine t-butyl ester (II-C) as an oil.

A mixture containing 13.72 gm (26.86 mmol) of compound (II-C) in 150 ml of 4N hydrogen chloride in dioxane under an atmosphere of nitrogen was stirred for 9 hours at room temperature. The mixture was concentrated in vacuo and the residue chromatographed on silica gel [20 cm×5.2 cm, hexanes→70% ether in hexanes] to afford 10.22 gm (84%) of N-[(1S)-1-ethoxycarbonyl-3-phenylpropyl]-N-(2,2,2-trichloroethoxy-carbonyl)-L-alanine (II-D) which solidified on standing: mp 73°–75° C.

A mixture of 46.8 gm (0.173 mol) of 2,4-dichloro-5-sulfamoylbenzoic acid in 400 ml of 5N ethanolic hydrogen chloride solution was stirred at room temperature for 64 hours. The reaction mixture was concentrated in vacuo and the product recrystallized from hot ether to yield 38.5 gms (75%) of ethyl 2,4-dichloro-5-sulfamoylbenzoate (II-E): mp 119°–122° C.

A mixture containing 29.9 gm (0.107 mol) of Nα-benzyloxycarbonyl-L-lysine, 30 ml of ethanol, and 9.0 ml of concentrated sulfuric acid in 250 ml of methylene chloride was refluxed for 22.5 hours. The reaction mixture was then cooled to room temperature and basified to pH of about 13 by the careful addition of a saturated aqueous solution of potassium carbonate. The aqueous phase was removed and the organic phase was washed one more time with a saturated potassium carbonate solution. The organic phase was dried over magnesium sulfate, filtered and concentrated in vacuo to give 29.8 gm (91%) of ethyl Nα-benzyloxycarbonyl-L-lysinate (II-F) as an oil.

A mixture containing 20.6 gm (66.8 mmol) of compound (II-F) and 8.50 gm (28.5 mmol) of compound (II-E) in 30 ml of tetrahydrofuran was refluxed for 51 hours. The reaction mixture was concentrated in vacuo to give a residue which was taken up in ethyl acetate and washed once with 10% aqueous acetic acid and once with water. The organic portion was dried over magnesium sulfate, filtered and concentrated in vacuo to give a viscous oil which was chromatographed via HPLC [Water's 500, 80% ether in hexanes, $k'=6.0$] to give 9.6 gm (59%) of a mixture of the two regioisomers: ethyl Nα-benzyloxycarbonyl-Nε-(5-chloro-2-ethoxycarbonyl-4-sulfamoylphenyl)-L-lysinate (II-Ga) (mp 86°–89° C.) and ethyl Nα-benzyloxycarbonyl-Nε-(5-chloro-4-ethoxycarbonyl-2-sulfamoylphenyl)-L-lysinate (II-Gb) (mp 140°–143° C.).

A mixture containing 10.2 gm (17.9 mmol) of a mixture of compounds (II-Ga) and (II-Gb) in 200 ml of 1.8M hydrogen bromide in glacial acetic acid was stirred at room temperature for 4.25 hours. The reaction mixture was diluted with 3.0 liters of ether and the precipitated product was collected and triturated with ether. The solidified product was filtered from the suspension to give 7.73 gm (84%) of a mixture of regioisomers: ethyl Nε-(5-chloro-2-ethoxycarbonyl-4-sulfamoylphenyl)-L-lysinate hydrobromide (II-Ha) and ethyl Nε-(5-chloro-4-ethoxycarbonyl-2-sulfamoylphenyl)-L-lysinate hydrobromide (II-Hb).

To a mixture containing 7.73 gm (15.0 mmol) of compounds (II-Ha) and (II-Hb) and 4.20 ml (30.1 mmol) of triethylamine in 100 ml of dry tetrahydrofuran at room temperature was added dropwise 2.00 ml (16.8 mmol) of benzyl bromide. The mixture was then refluxed for 7.5 hours after which it was filtered and concentrated in vacuo. The residue was chromatographed via HPLC [Water's 500, 15% ether in methylene chloride] to give separately 1.5 gm (19%) of ethyl Nα-benzyl-Nε-(5-chloro-2-ethoxycarbonyl-4-sulfamoylphenyl)-L-lysinate (II-I) ($k'=3.3$) and 1.5 gm (19%) of ethyl Nα-benzyl-Nε-(5-chloro-4-ethoxycarbonyl-2-sulfamoylphenyl)-L-lysinate (II-J) ($k'=7.4$).

To a mixture containing 728 mg (1.60 mmol) of compound (II-D) in 10 ml of dry methylene chloride at room temperature and under an atmosphere of nitrogen was added dropwise 0.40 ml (4.59 mmol) of oxalyl chloride followed by 10 μL (0.13 mmol) of N,N-dimethylformamide. The object of this step was to convert compound (II-D) to its acid chloride. After 3.5 hours the reaction mixture was concentrated in vacuo and the resultant acid chloride was dissolved in 3 ml of dry methylene chloride. To this mixture was then added dropwise a solution containing 820 mg (1.56 mmol) of compound (II-I) and 0.250 ml (1.79 mmol) of triethylamine in 6 ml of dry methylene chloride. After 1 hour the reaction mixture was taken up in methylene chloride and washed three times with 1N aqueous hydrochloric acid, once with a saturated aqueous solution of sodium bicarbonate, and once with brine. The organic portion was dried over magnesium sulfate, filtered, and concentrated in vacuo to give crude ethyl Nα-benzyl-Nα-[N-[(1S)-1-ethoxycarbonyl-3-phenylpropyl]-N-(2,2,2-trichloroethoxycarbonyl)-L-alanyl]-Nϵ-(5-chloro-2-ethoxycarbonyl-4-sulfamoylphenyl)-L-lysinate, which was utilized directly in the next step without further purification. The crude product dissolved in 10 ml of glacial acetic acid and under an atmosphere of nitrogen was treated with 1.20 gms (18.4 mmol) of zinc dust. After 1.75 hours the suspension was filtered through celite and concentrated in vacuo. The residue was taken up in methylene chloride and washed three times with a saturated aqueous solution of sodium bicarbonate and once with brine. The organic portion was dried over magnesium sulfate, filtered, and concentrated in vacuo. The product was chromatographed via HPLC [Water's 500, 55% ethyl acetate in hexanes, k'=4.5] to give 509 mg (41%) of ethyl Nα-benzyl-Nα-[N-[(1S)-1-ethoxycarbonyl-3-phenylpropyl]-L-alanyl]-Nϵ-(5-chloro-2-ethoxycarbonyl-4-sulfamoylphenyl)-L-lysinate (II-Kb). Treatment of this compound with etheral hydrogen chloride afforded 443 mg of its hydrochloride salt (II-K) as a white solid: mp 103°-107° C. (softens).

A mixture of 326 mg (0.396 mmol) of compound (II-K) and 3.0 ml of 1.0N (3.0 mmol) aqueous sodium hydroxide in 3 ml of ethanol was stirred at room temperature for 22 hours. The reaction mixture was acidified to pH 1 with 1.0N aqueous hydrochloric acid and then extracted four times with ethyl acetate. The organic portions were combined, washed once with brine, dried over magnesium sulfate, filtered, and concentrated in vacuo. The residue was triturated with ether and filtered to give 291 mg (99%) of Nα-benzyl-Nα-[N-[(1S)-1-carboxy-3-phenylpropyl]-L-alanyl]-Nϵ-(2-carboxy-5-chloro-4-sulfamoylphenyl)-L-lysine hydrochloride (II-L) as a white solid: mp 172°-176° C. (softens).

The reaction sequence was as follows:

(II-I) + (II-D) ⟶

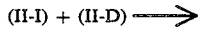
(II-K)

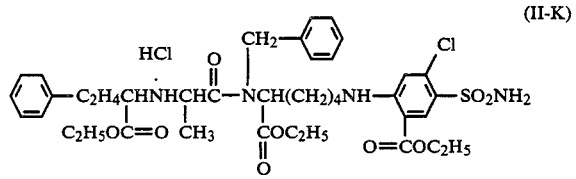

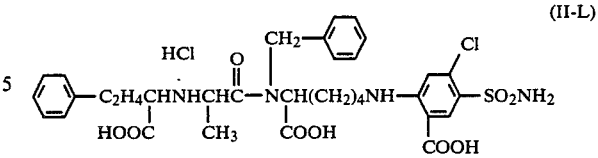
(II-L)

EXAMPLE III

Compound (II-D) and compound (II-J) were reacted with the identical sequence of reaction and isolation steps, and using the identical conditions and reagents, as were used to produce compound (II-K). The product, compound (III-A), was the hydrochloride salt of ethyl Nα-benzyl-Nα-[N-[(1S)-1-ethoxycarbonyl-3-phenylpropyl]-L-alanyl]-Nϵ-(5-chloro-4-ethoxycarbonyl-2-sulfamoylphenyl)-L-lysinate, a white solid mp 102°-106° C. (softens).

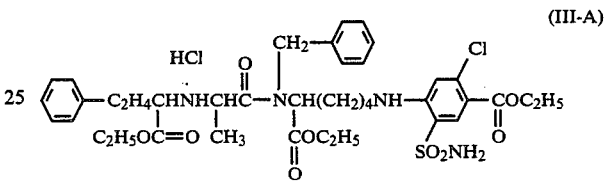
(III-A)

Compound (III-A) was reacted with sodium hydroxide and then hydrochloric acid, under the identical conditions to which compound (II-K) was subjected, to produce compound (III-B), Nα-benzyl-Nα-[N-[(1S)-1-carboxy-3-phenylpropyl]-L-alanyl]-Nϵ-(4-carboxy-5-chloro-2-sulfamoylphenyl)-L-lysine hydrochloride, a white solid mp 163°-165° C. (softens).

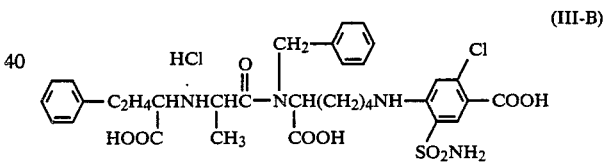
(III-B)

EXAMPLE IV

Into two separate 500 ml hydrogenation vessels each containing 100 ml of dioxane and 9.0 ml (160 mmol) of concentrated sulfuric acid was placed 11.0 gm (39.2 mmol) and 10.6 gm (37.8 mmol) of Nϵ-benzyloxycarbonyl-L-lysine. The two solutions were cooled to −78° C. and 140 ml of condensed (−78° C.) isobutylene was added to each vessel. The mixtures were then mechanically shaken (Parr shaker) at room temperature for 4 hours (26 psi). The reaction mixtures were combined and poured into 1000 ml (1.0 mol) of an ice cold solution of 1.0N aqueous sodium hydroxide and subsequently extracted three times with ether. The organic portions were combined (ca. 3000 ml), washed once with brine, dried over magnesium sulfate, filtered and concentrated in vacuo to give 16.7 gm (64%) of t-butyl Nϵ-benzyloxycarbonyl-L-lysinate (IV-A) as an oil.

To a solution containing 20.1 gms (59.7 mmol) of compound (IV-A) and 4.80 ml (59.3 mmol) of pyridine in 150 ml of dry tetrahydrofuran at −5° C. and under an atmosphere of nitrogen was added dropwise over a 15 minute period 8.50 ml (60.2 mmol) of trifluoroacetic anhydride. The reaction mixture was slowly allowed to warm to room temperature. After 16 hours the mixture was concentrated in vacuo. The residue was taken up in ether and washed twice with 1.0N aqueous hydrochloric acid, twice with a saturated aqueous solution of sodium bicarbonate, and once with brine. The organic portion was dried over magnesium sulfate, filtered, and concentrated in vacuo to afford a solid which was recrystallized from ether/hexanes to give 20.1 gm (78%) of t-butyl Nε-benzyloxycarbonyl-Nα-trifluoroacetyl-L-lysinate (IV-B): mp 77°–79° C.

A mixture of 24.7 gm (57.1 mmol) of compound (IV-B) and 2.87 gm of 10% palladium on activated carbon in 250 ml of absolute ethanol was hydrogenated at 55 psi for 2 hours. The mixture was filtered through celite and the filtrate concentrated in vacuo to give 17.0 gm (100%) of t-butyl Nα-trifluoroacetyl-L-lysinate (IV-C) as a viscous oil.

To a mixture containing 17.7 gm (59.3 mmol) of compound (IV-C) and 18.0 ml (129 mmol) of triethylamine in 100 ml of dry tetrahydrofuran at −5° C. and under an atmosphere of nitrogen was added dropwise over a 30 minute period a solution of 15.4 gm (60.7 mmol) of 4-chloro-3-sulfamoylbenzoyl chloride in 70 ml of dry tetrahydrofuran. The solution was slowly allowed to warm to room temperature. After 64 hours the mixture was concentrated in vacuo. The residue was taken up in ethyl acetate and washed twice with 1.0N aqueous hydrochloric acid, twice with a saturated aqueous solution of sodium bicarbonate, and once with brine. The organic portion was dried over magnesium sulfate, filtered, and concentrated in vacuo to afford an oil which was chromatographed via HPLC [Water's, 500, 50% ethyl acetate in hexanes, k′=3.0] to yield 16.8 gm (55%) of t-butyl Nε-(4-chloro-3-sulfamoylbenzoyl)-Nα-trifluoroacetyl-L-lysinate (IV-D) as a glass.

A mixture containing 11.10 gm (21.51 mmol) of compound (IV-D) and 53.0 ml (53.0 mmol) of 1.0N aqueous sodium hydroxide in 50 ml of ethanol was stirred at room temperature for 5 hours. The reaction was quenched by the addition of 80 ml (80.0 mmol) of 1.0N aqueous hydrochloric acid. The mixture was brought to pH=9 by the careful addition of a saturated aqueous solution of sodium bicarbonate and then was extracted three times with ethyl acetate. The organic portions were combined (ca. 500 ml), washed once with brine, dried over magnesium sulfate, filtered, and concentrated in vacuo. The product was recrystallized from ethyl acetate/hexanes to yield 6.74 gm (75%) of t-butyl Nε-(4-chloro-3-sulfamoylbenzoyl)-L-lysinate (IV-E) as a white solid: mp 158°–160° C.

A mixture containing 8.38 gm (19.1 mmol) of compound (IV-E), 34.1 gm (173 mmol) of 2-bromoindane, and 13.3 gm (158 mmol) of sodium bicarbonate in 130 ml of acetonitrile under an atomosphere of nitrogen was refluxed for 48 hours. The reaction mixture was concentrated in vacuo and the residue taken up in ethyl acetate and washed twice with water and once with brine. It was dried over magnesium sulfate, filtered, and concentrated in vacuo. The residue was chromatographed via HPLC [Water's 500, 70% ethyl acetate in hexanes, k′=3.8] to give 8.39 gm (82%) of t-butyl Nε-(4-chloro-3-sulfamoylbenzoyl)-Nα-(2,3-dihydro-1H-inden-2-yl)-L-lysinate (IV-F): mp 65°–68° C.; $[\alpha]_D^{MeOH} = +14.7°$.

To a mixture containing 4.64 gm (10.2 mmol) of product (II-D) in 40 ml of dry methylene chloride at room temperature and under an atmosphere of nitrogen was added dropwise 7.30 ml (83.8 mmol) of oxalyl chloride followed by 30 μL (0.39 mmol) of N,N-dimethylformamide. After 3.5 hours the reaction mixture was concentrated in vacuo. The residue (ca. 4.9 gm) was dissolved in 25 ml of dry methylene chloride, placed under an atmosphere of nitrogen, and cooled to −5° C. To this mixture was then added dropwise over a 25 minute period a solution of 3.98 gm (7.42 mmol) of compound (IV-F) and 7.50 ml (53.8 mmol) of triethylamine in 40 ml of dry methylene chloride. The solution was slowly allowed to warm to room temperature. After 15.25 hours the reaction mixture was concentrated in vacuo. The residue was taken up in ethyl acetate and washed four times with 1.0N aqueous hydrochloric acid (ca. 1000 ml) and once with brine. It was dried over magnesium sulfate, filtered, and concentrated in vacuo. The product was chromatographed via HPLC [Water's 500, 7% acetic acid in ethyl acetate, k′=5.8] to give 5.02 gm (70%) of t-butyl Nε-(4-chloro-3-sulfamoylbenzoyl)-Nα-(2,3-dihydro-1H-inden-2-yl)-Nα-[N-[(1S)-1-ethoxycarbonyl-3-phenylpropyl]-N-(2,2,2-trichloroethoxycarbonyl)-L-alanyl]-L-lysinate (IV-G) as a glass.

A mixture of 5.02 gm (5.16 mmol) of compound (IV-G) in 25 ml of glacial acetic acid at room temperature and under an atmosphere of nitrogen was treated with 9.80 gm (150 mmol) of zinc dust. After 7 hours the suspension was filtered through celite and the filtrate was concentrated in vacuo. Trituration of the residue with ether afforded 4.71 gm of a solid which was dissolved in a saturated aqueous solution of sodium bicarbonate. The solution was then extracted three times with ethyl acetate. The organic portions were combined, washed once with brine, dried over magnesium sulfate, filtered, and concentrated in vacuo. The product was chromatographed via HPLC [Water's 500, ethyl acetate/hexanes/methanol (5/4/1), k′=2.7] to afford t-butyl Nε-(4-chloro-3-sulfamoylbenzoyl)-Nα-(2,3-dihydro-1H-inden-2-yl)-Nα-[N-[(1S)-1-ethoxycarbonyl-3-phenylpropyl]-L-alanyl]-L-lysinate. Treatment of this compound with etheral hydrogen chloride yielded 2.88 gm (67%) of its hydrochloride salt (IV-H) as a white solid.

A mixture containing 1.14 gm (1.36 mmol) of compound (IV-H) in 50 ml of 4N hydrogen chloride in dioxane at room temperature and under an atmosphere of nitrogen was stirred for 17 hours. The mixture was concentrated in vacuo and the residue was triturated with hexanes, filtered off and dried (T about 70° C.) under vacuum to give 844 mg (80% of Nε-(4-chloro-3-sulfamoylbenzoyl)-Nα-(2,3-dihydro-1H-inden-2-yl)-Nα-[N-[(1S)-1-ethoxycarbonyl-3-phenylpropyl]-L-alanyl]-L-lysine hydrochloride (IV-I) as a white solid: mp 158°–162° C. (softens).

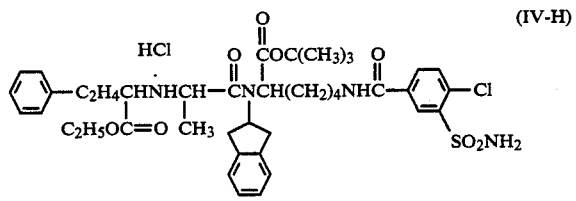

(IV-H)

-continued

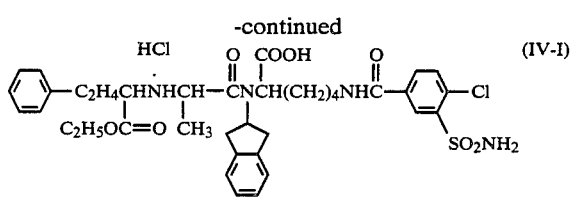

(IV-I)

EXAMPLE V

A solution of sodium bisulfite (72.8 g, 0.70 m) in water (390 ml) was added dropwise to a boiling mixture of 4-chloro-3-nitro-5-sulfamylbenzoic acid (38.6 g, 0.14 m) in water (390 ml). The mixture was then refluxed 1 hour, acidified to pH 2 with concentrated hydrochloric acid, and refluxed another 30 minutes. On cooling a white precipitate formed which was collected and washed with water. Yield: 23.9 g (68%) of 3-amino-4-chloro-5-sulfamoylbenzoic acid (V-A).

Compound (V-A) (10.0 g, 0.040 m) was dissolved in ethanol (100 ml)/sulfuric acid (1.5 ml) and refluxed for 5 hours. The solution was concentrated in vacuo and the residue treated with saturated sodium bicarbonate solution. The resulting solid was collected, washed with water and recrystallized from aqueous ethanol. Yield: 6.8 g (61%) of ethyl 3-amino-4-chloro-5-sulfamoyl benzoate (V-B).

Disodium iminodiacetate monohydrate (11.7 g, 0.060 m) was dissolved in water (40 ml) and cooled to 0°. Benzyl chloroformate (13.3 g, 0.078 m) was added in portions as the pH of the solution was kept at 9–12 by addition of 2N sodium hydroxide solution as needed. When addition was complete the mixture was stirred an additional 3 hours at 0°–10° C., then extracted with diethyl ether. The aqueous layer was acidified with concentrated hydrochloric acid and extracted with ethyl acetate. The organic layer was separated, dried over sodium sulfate and concentrated to give 13.0 g (81%) of N-benzyloxycarbonyliminodiacetic acid (V-C).

Compound (V-C) (6.3 g, 24 mmol) and acetic anhydride (13.0 g, 0.127 m), were combined and stirred 2 days at room temperature. Acetic acid and anhydride were removed in vacuo and the residue was recrystallized from hexanes/ethyl acetate to give 7.2 g (78%) of N-benzyloxycarbonyliminodiacetic anhydride (V-D).

Compound (V-B) (5.6 g, 20 mmol) and compound (V-D) (5.5 g, 22 mmol) were dissolved in acetonitrile (80 ml) and stirred 3 days. The mixture was then filtered to give the desired product. Additional material of lower purity could be obtained by concentrating the filtrate and washing the brown residue with hexane/ethyl acetate. Total yield: 10.1 g (96%) of ethyl 3-[N-benzyloxycarbonyl-N-(carboxymethyl)-glycinamido]-4-chloro-5-sulfamoylbenzoate (V-E).

Compound (V-E) (10.1 g, 19.1 mmol) was combined with acetic acid containing 32% hydrogen bromide (60 ml total) and allowed to stand 1.75 hours. The slurry was then washed several times with ether and dried in vacuo at 80° C. to give ethyl 3-[N-(carboxymethyl)-glycinamido]-4-chloro-5-sulfamoylbenzoate hydrobromide (8.1 g, 89%). This material was dissolved in water (70 ml), the solution was filtered and neutralized with 1N sodium hydroxide solution (17 ml). The resulting precipitate was collected and washed with water and ethanol to give 6.1 g (91%) of ethyl 3-[N-(carboxymethyl)glycinamido]-4-chloro-5-sulfamoyl benzoate (V-F).

A solution of compound (V-F) (6.1 g, 15 mmol) in ethanol (125 ml) containing sulfuric acid (1 ml) was refluxed 24 hours and then concentrated in vacuo. Sodium bicarbonate solution was added and the precipitate was collected and washed with water. Yield: 5.7 g (87%) of ethyl 3-[N-ethoxycarbonylmethyl)-glycinamido]-4-chloro-5-sulfamoyl benzoate (V-G).

A solution of compound (V-G) (2.97 g, 7.04 mmol) and triethylamine (0.819 g, 8.09 mmol) in dry tetrahydrofuran (100 ml) was added to a solution of 7.04 mmol of the acid chloride of compound (II-D) (see Example II) in 50 ml of tetrahydrofuran. After stirring overnight, the mixture was filtered and the filtrate was diluted with water until a second phase formed. The mixture was extracted with methylene chloride and the organic portion washed with 1N HCl, saturated sodium bicarbonate solution, and brine. After drying over sodium sulfate, the solution was concentrated in vacuo to provide 58 g (yield 96%) of a white foam, ethyl N-[N-[(1S)-1-ethoxycarbonyl-3-phenylpropyl]-N(2,2,2-trichloroethoxycarbonyl)-L-alanyl]-N-[N-(2-chloro-5-ethoxycarbonyl-3-sulfamoylphenyl)-2-aminocarbonylmethyl]-glycinate (V-H).

Compound (V-H) (5.8 g, 6.7 mmol) was dissolved in acetic acid and zinc dust (5.9 g, 90 mmol) was added. The mixture was stirred vigorously for 4 hours, then filtered through celite. The filtrate was concentrated and residual acetic acid was azeotroped off with toluene. The residue was dissolved in ethyl acetate and the solution was washed with saturated sodium bicarbonate solution, water, and brine. The organic portion was dried over sodium sulfate and concentrated in vacuo to a foam, ethyl N-[N-[(1S)-1-ethoxycarbonyl-3-phenylpropyl]-L-alanyl]-N-[N-(2-chloro-5-ethoxycarbonyl-3-sulfamoylphenyl)-2-aminocarbonylmethyl]glycinate (V-I).

Sodium hydroxide (0.146 g, 3.65 mmol) in water (0.3 ml) was added to a solution of compound (V-I) (0.486 g, 0.71 mmol) in 3.0 ml of methanol. The solution was stirred two hours, then concentrated in vacuo at room temperature. The residue was dissolved in water and the solution was neutralized with concentrated HCl, whereupon a white precipitate formed. Filtration gave 0.24 g (yield: 56%) of N-[N-[(1S)-1-carboxy-3-phenylpropyl]-L-alanyl]-N-[N-(2-chloro-5-carboxy-3-sulfamoylphenyl)-2-aminocarbonylmethyl]glycine (V-J).

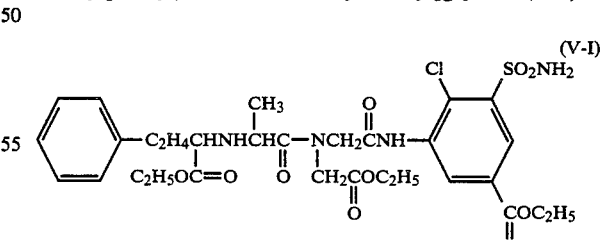

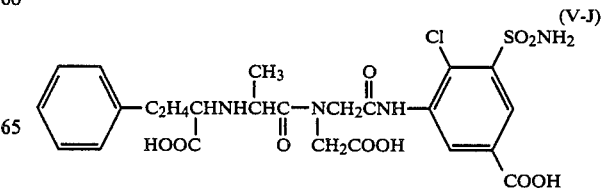

EXAMPLE VI

A mixture of 3-nitro-4-phenoxy-5-sulfamylbenzoic acid (3.7 g, 0.011 mol), 10% palladium on carbon (0.5 g) and ethanol (100 ml) was shaken on a Parr hydrogenator for 1.5 hours at a hydrogen pressure of 40 psi. The catalyst was filtered off and the filtrate was concentrated to a white solid. Yield: 3.2 g (94%) of 3-amino-4-phenoxy-5-sulfamoylbenzoic acid (VI-A).

A mixture of compound (VI-A) (6.17 g, 0.020 mmol), 2-nitroethyl acetate (2.66 g, 0.020 mmol), sodium acetate trihydrate (2.72 g, 0.020 mol), acetic acid (1.20 g, 0.020 mol) and water (6 ml) was heated to 75° over 20 minutes, then cooled. The precipitate was filtered and washed with water and ethanol to give 3.93 g (51.5%) of compound (VI-B), 3-(2-nitroethylamino)-4-phenoxy-5-sulfamoylbenzoic acid.

Compound (VI-B) (4.0 g, 10 mmol) and a catalytic amount of Raney Nickel were slurried in water (90 ml)/ethanol (90 ml). The mixture was hydrogenated on a Parr apparatus for 3.5 hours at an initial pressure of 51 psi. The mixture was then filtered and the precipitate was extracted several times with hot water. The filtrate and extracts were combined and concentrated to yield 3.6 g (97%) of compound (VI-C), 3-(2-aminoethylamino)-4-phenoxy-5-sulfamoylbenzoic acid.

Compound (VI-C) (4.4 g, 12 mmol) was added to ethanol (150 ml), followed by sulfuric acid (1.5 ml). The solution was refluxed 18 hours, then concentrated in vacuo. The residue was dissolved in water and neutralized with sodium bicarbonate solution, then extracted with ethyl acetate. The organic layer was washed with brine, dried over sodium sulfate and concentrated to give 4.0 g (84%) of compound (VI-D), ethyl 3-(2-aminoethylamino)-4-phenoxy-5-sulfamoylbenzoate.

A mixture of bromoacetic acid (34.8 g, 0.25 mol), benzyl alcohol (27.0 g, 0.25 mol), p-toluenesulfonic acid (3 g, 0.02 mol) and cyclohexane (200 ml) and cyclohexane (200 ml) was refluxed 6 hours in a flask equipped with a Dean Stark trap, condenser and mechanical stirrer. The mixture was cooled and stirred 10 minutes with saturated sodium bicarbonate solution (150 ml). The organic layer was then extracted four more times with saturated sodium bicarbonate solution, washed with water and brine, then concentrated in vacuo. The yield of benzyl bromoacetate was quantitative.

A solution of compound (VI-D) (2.8 g, 7.4 mmol) and triethylamine (1.0 g, 10 mmol) in tetrahydrofuran (100 ml) was cooled to 0°. Benzyl bromoacetate (1.9 g, 8.1 mmol) was added and the solution was allowed to stir at room temperature for 2 days. The mixture was filtered and the filtrate was concentrated in vacuo. The residue was purified by high-pressure liquid chromatography to provide compound (VI-E), ethyl 3-[2-[N-(benzyloxycarbonylmethyl)amino]-ethylamino]-4-phenoxy-5-sulfamoyl benzoate. Proceeding via the t-butyl analog of this benzyl compound gives satisfactory results.

A solution of compound (VI-E) (0.93 g, 1.8 mmol) and triethylamine (0.20 g, 2.0 mmol) in tetrahydrofuran (25 ml) was added in one portion to 1.76 mmol of the acid chloride of compound (II-D) (see Example II) in tetrahydrofuran (10 ml). The mixture was stirred 2 hours and then filtered. The filtrate was diluted with an equal amount of water and the mixture was extracted with methylene chloride. The organic layer was separated, washed with water and brine, and dried over sodium sulfate. Concentration gave a foam (1.39 g, 82%) of compound (VI-F), benzyl N-[N-[(1S)-1-ethoxycarbonyl-3-phenylpropyl]-N-(2,2,2-trichloroethoxycarbonyl)-L-alanyl]-N-[N-(2-phenoxy-5-ethoxycarbonyl-3-sulfamoylphenyl)-2-aminoethyl]glycinate.

The —CO$_2$CH$_2$CCl$_3$ protecting group was removed from compound (VI-F) by dissolving 1.0 g (1.0 mmol) of compound (VI-F) in 6.9 ml of acetic acid and adding zinc dust (0.91 g, 14 mmol). The mixture was stirred 4 hours and filtered. The filtrate was concentrated in vacuo. The residue was purified by column chromatography to give compound (VI-G), benzyl N-[N-[(1S)-1-ethoxycarbonyl-3-phenylpropyl]-L-alanyl]-N-[N-(2-phenoxy-5-ethoxycarbonyl-3-sulfamoylphenyl)-2-aminoethyl]glycinate.

Compound (VI-G) is dissolved in ethanol and a catalytic amount of 10% palladium on carbon is added. The mixture is hydrogenated for 6 hours at an initial hydrogen pressure of 50 psi. The catalyst is filtered off and the filtrate concentrated to give the product (VI-H), N-[N-[(1S)-1-ethoxycarbonyl-3-phenylpropyl]-L-alanyl]-N-[N-(2-phenoxy-5-ethoxycarbonyl-3-sulfamoylphenyl)-2-aminoethyl]glycine.

Compound (VI-H) is added to an aqueous solution of sodium hydroxide in methanol. The mixture is stirred 2 hours, then concentrated in vacuo. The residue is dissolved in water and neutralized with concentrated hydrochloric acid. The resulting precipitate is collected, providing compound (VI-I), N-[N-[(1S)-1-carboxy-3-phenylpropyl]-L-alanyl]-N-[N-(2-phenoxy-5-carboxy-3-sulfamoylphenyl)-2-aminoethyl]glycine.

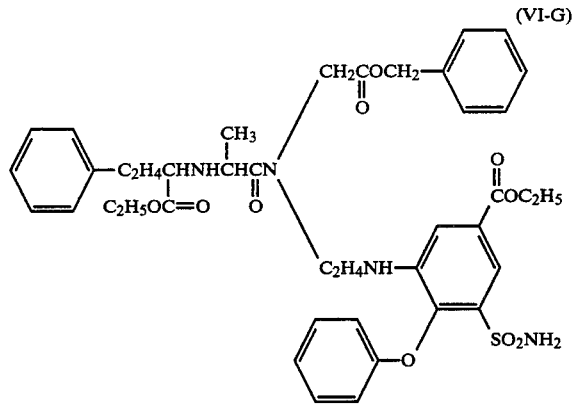

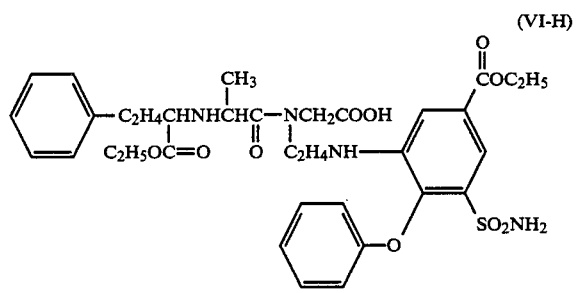

-continued

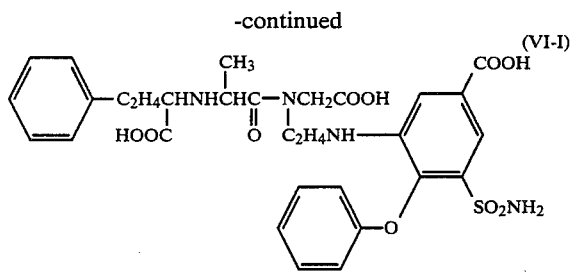
(VI-I)

EXAMPLES VII–XIV

The following compounds are made by procedures analogous to the aforementioned and within the skill of the art.

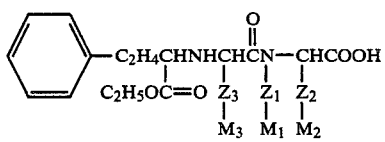

| EXAMPLE | COMPOUND | $-Z_1M_1$ | $-Z_2M_2$ | $-Z_3M_3$ |
|---|---|---|---|---|
| VII | 1-[N—[(1S)—1-ethoxy-carbonyl-3-phenyl-propyl]-L-alanyl]-1-carboxymethyl-2-(2-amino-4-chloro-5-sulfamoylbenzoyl) hydrazine | —NHC(O)— phenyl with SO$_2$NH$_2$, Cl, NH$_2$ | —H | —CH$_3$ |
| VIII | 1-[N—[(1S)—1-ethoxy-carbonyl-3-phenyl-propyl]-L-alanyl]-1-carboxymethyl-2-(2-chloro-3-sulfamoyl-5-ethoxycarbonyl-phenyl) hydrazine | —NH— phenyl with COC$_2$H$_5$, Cl, SO$_2$NH$_2$ | —H | —CH$_3$ |
| IX | N—[N—[(1S)—1-ethoxy-carbonyl-3-phenyl-propyl]-L-alanyl]-N—[N—(2-chloro-3-sulfamoyl-5-ethoxycarbonylphenyl)-4-aminobutyl]glycine | —(CH$_2$)$_4$NH— phenyl with COC$_2$H$_5$, Cl, SO$_2$NH$_2$ | —H | —CH$_3$ |
| X | 6-Chloro-3,4-dihydro-3-[N—(carboxy-methyl)-N—[N—[(1S)—1-ethoxycarbonyl-3-phenylpropyl]-L-alanyl]aminomethyl]-7-sulfamoyl-2H—1,2,4-benzothiadiazine-1,1-dioxide | —CH$_2$CH with NH—SO$_2$ and NH-phenyl(Cl, SO$_2$NH$_2$) ring | —H | —CH$_3$ |
| XI | Nε-(2-Amino-4-chloro-5-sulfamoylbenzoyl)-Nα-benzyl-Nα-[N—[(1S)—1-ethoxycarbonyl-3-phenylpropyl]-L-alanyl]-L-lysine | —CH$_2$— phenyl | —(CH$_2$)$_4$NHC(O)— phenyl with SO$_2$NH$_2$, Cl, NH$_2$ | —CH$_3$ |
| XII | Nα-Benzyl-Nα-[N—[(1S)—1-ethoxycarbonyl-3-phenylpropyl]-L-alanyl]-Nε-(5-chloro-2-ethoxycarbonyl-4-sulfamoylphenyl)-L-lysine | —CH$_2$— phenyl | —(CH$_2$)$_4$NH— phenyl with Cl, SO$_2$NH$_2$, C$_2$H$_5$OC=O | —CH$_3$ |
| XIII | N—(5-t-butyl-2-hydroxyl-3-iodobenzyl)-N—[N—[(1S)—1-ethoxy-carbonyl-3-phenyl-propyl]-L-alanyl]-glycine | —CH$_2$— phenyl with OH, I, C(CH$_3$)$_3$ | —H | —CH$_3$ |

$-Z_1M_1-Z_2M_2-$

-continued

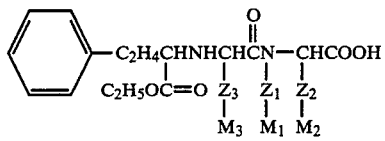

| | | | |
|---|---|---|---|
| XIV | N—[Nα-[(1S)—1-ethoxy-carbonyl-3-phenyl-propyl]-Nε-[2-amino-4-chloro-5-sulfamoylbenzoyl]-L-lysyl]-L-proline | —(CH₂)₃— | 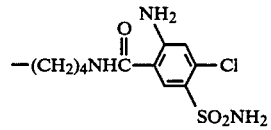 |

EXAMPLES XV-XVI

| | |
|---|---|
| XV | 6-Chloro-3,4-dihydro-3-[N—(ethoxycarbonylmethyl)-N—[N'—[(1S)—1-ethoxycarbonyl-3-phenylpropyl]-L-alanyl]-aminomethyl]-7-sulfamoyl-2H—1,2,4-benzothiadiazine-1,1-dioxide |
| XVI | 6-Chloro-3,4-dihydro-3-[N—(carboxymethyl)-N—[N'—[1-carboxy-3-phenylpropyl]-L-alanyl]-aminomethyl]-7-sulfamoyl-2H—1,2,4-benzothiadiazine-1,1-dioxide hydrochloride |

What is claimed is:

1. Compounds having the formula

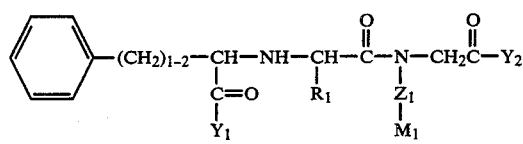

and pharmaceutically acceptable salts thereof, wherein
m is 1 or 2;
$Y_1$ and $Y_2$ are independently —OH or alkoxy containing 1 to 6 carbon atoms;
$R_1$ is hydrogen, alkyl containing 1 to 6 carbon atoms, or amino-alkyl containing 1 to 6 carbon atoms;
—$Z_1M_1$ is

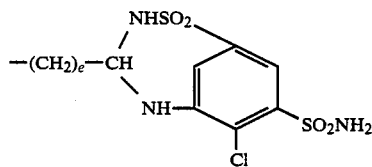

and e is 1–4.

2. The compounds and salts of claim 1 wherein there is at least one asymmetric carbon, and the substituents on each asymmetric carbon are in the "S" configuration.

3. The compounds according to claim 1 wherein m is 2; $Y_1$ and $Y_2$ are —OH; $R_1$ is methyl; and e is 3; and its pharmaceutically acceptable salts.

4. The compound according to claim 1 wherein m is 2; $Y_1$ and $Y_2$ are —OH; $R_1$ is omega-amino-n-butyl; and e is 1; and its pharmaceutically acceptable salts.

5. The compound according to claim 1 which is 6-Chloro-3,4-dihydro-3-[N-(carboxymethyl)-N-[N'-[1-carboxy-3-phenylpropyl]-L-alanyl]-aminomethyl]-7-sulfamoyl-2H-1,2,4-benzothiadiazine-1,1-dioxide hydrochloride, and pharmaceutically acceptable salts thereof.

6. A pharmaceutical preparation having angiontensin converting enzyme inhibitory activity comprising an angiotensin converting enzyme inhibitory amount of a compound or salt according to claim 1 in association with a pharmaceutically acceptable carrier.

7. The method of alleviating hypertension in a mammal in need of treatment therefor, comprising administering to said mammal an antihypertensive effective amount of a compound or salt according to claim 1.

* * * * *